United States Patent [19]

Lilburn

[11] 4,234,321
[45] Nov. 18, 1980

[54] FUEL COMPOSITIONS CONTAINING DEPOSIT CONTROL ADDITIVES

[75] Inventor: Jennifer E. Lilburn, Berkeley, Calif.

[73] Assignee: Chevron Research Company, San Francisco, Calif.

[21] Appl. No.: 931,233

[22] Filed: Aug. 8, 1978

[51] Int. Cl.$^3$ .............................................. C10L 1/22
[52] U.S. Cl. ............................................ 44/72; 44/77
[58] Field of Search ................. 44/72, 77; 260/482 B, 260/482 C

[56] References Cited

U.S. PATENT DOCUMENTS 4,105,417  8/1978  Coon ........................................ 44/72

FOREIGN PATENT DOCUMENTS 855961  7/1977  Belgium .
855962  7/1977  Belgium .

Primary Examiner—Jacqueline V. Howard
Attorney, Agent, or Firm—D. A. Newell; S. R. LaPaglia

[57] ABSTRACT

Fuel compositions are provided which contain a deposit control additive. The deposit control additive is produced by reacting a hydrocarbylpoly(oxyalkylene) alcohol with excess phosgene and an excess amount of certain polyamines. The product comprises hydrocarbylpoly(oxyalkylene) ureylene carbamates.

23 Claims, No Drawings

FUEL COMPOSITIONS CONTAINING DEPOSIT CONTROL ADDITIVES

BACKGROUND OF THE INVENTION

1. Field of the Invention

In recent years, numerous fuel detergents or "deposit control" additives have been developed. These materials when added to hydrocarbon fuels employed in internal combustion engines effectively reduce deposit formation which ordinarily occurs in carburetor ports, throttle bodies, venturis, intake ports and intake valves. The reduction of these deposit levels has resulted in increased engine efficiency and a reduction in the level of hydrocarbon and carbon monoxide emissions.

A complicating factor has, however, recently arisen. With the advent of automobile engines that require the use of non-leaded gasolines (to prevent disablement of catalytic converters used to reduce emissions), it has been found difficult to provide gasoline of high enough octane to prevent knocking and the concomitant damage which it causes. The difficulty is caused by octane requirement increase, herein called "ORI", which is due to deposits formed in the combustion chamber while the engine is operating on commercial gasoline.

The basis of the ORI problem is as follows: each engine, when new, requires a certain minimum octane fuel in order to operate satisfactorily without pinging and/or knocking. As the engine is operated on any gasoline, this minimum octane increases and, in most cases, if the engine is operated on the same fuel for a prolonged period will reach equilibrium. This is apparently caused by an amount of deposits in the combustion chamber. Equilibrium is typically reached after 5000 to 15,000 miles of automobile operation.

The octane requirements increase measured in a particular engine, using commercial gasolines, will vary from 5 to 6 octane units, at equilibrium, to as high as 12 or 15 units, depending upon the gasoline compositions, engine design and type of operation. The seriousness of the problem is thus apparent. A typical 1975 or 1976 automobile with a research octane requirement of 85 when new may after a few months of operation require 97 research octane gasoline for proper operation, and little unleaded gasoline of that octane is available. The ORI problem exists in some degree with engines operated on leaded fuels. U.S. Pat. Nos. 3,144,311 and 3,146,203 disclose lead-containing fuel compositions having reduced ORI properties.

It is believed, however, by many experts that the ORI problem, while present with leaded gasolines, is much more serious with unleaded fuel because of the different nature of the deposits formed with the respective fuels, the size of increase, and because of the lesser availability of high-octane non-leaded fuels. This problem is compounded by the fact that the most common means of enhancing the octane of unleaded gasoline, increasing its aromatic content, also appears to increase the eventual octane requirement of the engine. Furthermore, some of the presently used nitrogen-containing deposit control additives with mineral oil or polymer carriers appear to contribute significantly to the ORI of engines operated on unleaded fuel.

It is, therefore, highly desirable to provide fuel compositions which contain deposit control additives which effectively control deposits in intake systems (carburetor, valves, etc.) of engines operated with fuels containing them, but do not contribute to the combustion chamber deposits which cause increased octane requirements. While, in general, deposit control fuel additives are not believed to be useful dispersants for lubricating oil compositions, certain additives of the present invention are useful in this regard.

2. Description of the Prior Art

Belgian Pat. Nos. 855,961 and 855,962 disclose and claim certain poly(oxyalkylene) aminocarbamates and their fuel compositions.

SUMMARY OF THE INVENTION

A process for the production of hydrocarbon-soluble additives provides a product suitable for use as a deposit control additive in fuels, or as a dispersant additive in lubricating oil compositions. The additive is the final product of the process comprising the steps of reacting, in a first step, a hydrocarbylpoly(oxyalkylene) alcohol with phosgene in the mol ratio of from about 1:1 to about 1:5 at a temperture of about 10° to 100° C. to obtain a first product; reacting, in a second step, said first product with a polyamine in a mol ratio of said alcohol to polyamine of from about 1:1.1 to about 1:20 at a temperature of about $-10°$ C. to 200° C. to obtain a second product; and reacting, in an optional third step, said second product with phosgene in such amount that the total phosgene reacted in all the steps of the process is in mol ratio to said alcohol of from about 1.1:1 to 5:1; wherein said hydrocarbylpoly(oxyalkylene) alcohol is composed of oxyalkylene units selected from 2 to 5 carbon oxyalkylene units of which at least a sufficient number are branched chain oxyalkylene units to render said final product soluble in fuel or lubricating oil compositions, said hydrocarbyl group contains from 1 to 30 carbon atoms, said polyamine contains 2 to 40 carbon atoms and from 2 to 12 amine nitrogen atoms and said polyamine consists, at least in part, of polyamine containing at least 2 primary or secondary amine nitrogen atoms. The final product of the process is a mixture comprising hydrocarbylpoly(oxyalkylene) ureylene carbamates having a molecular weight from about 600 to about 10,000, and preferably having at least one basic nitrogen atom.

DETAILED DESCRIPTION OF THE INVENTION

The final product of this process of making certain deposit control fuel additives is a complex mixture of carbamates which is believed to comprise hydrocarbylpoly(oxyalkylene) aminocarbamates, hydrocarbylpoly(oxyalkylene) amino-bis-carbamates and dicarbamates, as well as, hydrocarbylpoly(oxyalkylene) imidazolidones and hydrocarbylpoly(oxyalkylene) ureylene carbamates. The final product may be used directly in fuel and lubricating oil compositions. In the process of the present invention, a hydrocarbylpoly(oxyalkylene) alcohol, i.e., a polyether alcohol, composed of oxyalkylene units selected from $C_2$–$C_5$ oxyalkylene units, at least a sufficient number of which are branched chain oxyalkylene units to render said product soluble in hydrocarbonaceous fuel and/or lubricating oil compositions, and wherein the hydrocarbyl group contains about 1–30 carbon atoms, is reacted with phosgene in mol ratio alcohol:phosgene of about 1:1 to 1:5, preferably 1:1 to 1:2.5, at about $-10°$ C. to 100° C. for a period of about 0.1 to 24 hours. In general, without further treatment, this first product is reacted with a polyamine in mol ratio alcohol:polyamine of about 1:1.1 to 1:20 at a temperature of about −10° C. to 200° C. The polyamine contains from 2 to 40 carbon atoms and from 2 to 12 amine nitrogen atoms, and said polyamine consists at least in part of polyamine containing at least two primary or secondary amine nitrogen atoms. If sufficient phosgene has been added in the process, the product of the second step may be used directly, generally without further treatment, as a fuel or lubricating oil additive. However, if the total amount of phosgene used in the process has been less than that specified, i.e., less phosgene than in mol ratio to alcohol of 1.1:1 to about 5:1, the product of the second step is reacted with phosgen in such amount that the total phosgene reacted in the process is in mol ratio to said alcohol as phosgene:alcohol of from about 1.1:1 to about 5:1, preferably from about 1.1:1 to about 2.5:1. The complex final product mixture comprising the aforementioned carbamates, and including ureylene carbamates such as the ureylene aminocarbamates may be used directly in fuel and lubricating oil compositions according to the present invention.

Preferred Polyamines

The polyamines finding use within the scope of this invention are those having from 2 to 12 amine nitrogen atoms and from 2 to about 40 carbon atoms. The polyamine preferably has a carbon-to-nitrogen ratio of from about 1:1 to about 10:1. Mixtures of polyamines may be used, but the polyamine is characterized in that it consists at least in part of polyamine containing at least two primary or secondary amine nitrogen atoms, i.e., at least about 5-10 mol percent of the polyamine consists of polyamine containing at least two primary or secondary amine nitrogen atoms.

The polyamine may be substituted with substituents selected from (A) hydrogen, (B) hydrocarbyl groups of from 1 to about 10 carbon atoms, (C) acyl groups of from 2 to about 10 carbon atoms, and (D) monoketo, monohydroxy, mononitro, monocyano, lower alkyl and lower alkoxy derivatives of (B) and (C). "Lower", as used in terms like lower alkyl or lower alkoxy, means a group containing from 1 to about 6 carbon atoms.

Hydrocarbyl, as used in describing all the components of this invention, denotes an organic radical composed of carbon and hydrogen which may be aliphatic, alicyclic, aromatic or combinations thereof, e.g., aralkyl. Preferably, the hydrocarbyl group will be relatively free of aliphatic unsaturation, i.e., ethylenic and acetylenic, particularly acetylenic unsaturation. The substituted polyamines of the present invention are generally, but not necessarily, N-substituted polyamines. Exemplary hydrocarbyl groups and substituted hydrocarbyl groups include alkyls such as methyl, ethyl, propyl, butyl, isobutyl, pentyl, hexyl, octyl, etc., alkenyls such as propenyl, isobutenyl, hexenyl, octenyl, etc., hydroxyalkyls, such as 2-hydroxyethyl, 3-hydroxylpropyl, hydroxy-isopropyl, 4-hydroxylbutyl, etc., ketoalkyls, such as 2-ketopropyl, 6-ketooctyl, etc., alkoxy and lower alkenoxy alkyls, such as ethoxyethyl, ethoxypropyl, propoxyethyl, propoxypropyl, etc. The aforementioned acyl groups (C) are such as propionyl, acetyl, etc. The more preferred substituents are hydrogen, $C_1$-$C_6$ alkyls and $C_1$-$C_6$ hydroxyalkyls.

In a substituted polyamine and substituents are found at any atom capable of receiving them. The substituted atoms, e.g., substituted nitrogen atoms, are generally geometrically equivalent, and consequently the substituted amines finding use in the present invention can be mixtures of mono- and poly- substituted polyamines with substituent groups situated at equivalent and/or inequivalent atoms.

The more preferred polyamine finding use within the scope of the present invention is a polyalkylene polyamine, including alkylene diamine, and including substituted polyamines, e.g., alkyl and hydroxyalkyl-substituted polyalkylene polyamine. Preferably, the alkylene group contains from 2 to 6 carbon atoms, there being preferably from 2 to 3 carbon atoms between the nitrogen atoms. Such groups are exemplified by ethylene, 1,2-propylene, b 2,2-dimethyl-propylene, trimethylene, 1,3,2-hydroxypropylene, etc. Examples of such polyamines include ethylene diamine, diethylene triamine, di(trimethylene)triamine, dipropylene triamine, triethylene tetraamine, tripropylene tetraamine, tetraethylene pentamine, and pentaethylene hexamine. Such amines encompass isomers such as branched-chain polyamines and the previously-mentioned substituted polyamines, including hydroxy- and hydrocarbyl-substituted polyamines. Among the polyalkylene polyamines, those containing 2–12 amine nitrogen atoms and 2–24 carbon atoms are especially preferred, and the $C_2$-$C_3$ alkylene polyamines are most preferred, in particular, the lower polyalkylene polyamines, e.g., ethylene diamine, dipropylene triamine, etc.

The amine component of the poly(oxyalkylene) amino-carbamate also may be derived from heterocyclic polyamines, heterocyclic substituted amines and substituted heterocyclic compounds, wherein the heterocycle comprises one or more 5–6 membered rings containing oxygen and/or nitrogen. Such heterocyclic rings may be saturated or unsaturated and substituted with groups selected from the aforementioned (A), (B), (C) and (D).

In many instances the amine used as a reactant in the production of the carbamate of the present invention is not a single compound but a mixture in which one or several compounds predominate with the average composition indicated. For example, tetraethylene pentamine prepared by the polymerization of aziridine or the reaction of dichloroethylene and ammonia will have both lower and higher amine members, e.g., triethylene tetraamine, substituted piperazines and pentaethylene hexamine, but the composition will be mainly tetraethylene pentamine and the empirical formula of the total amine composition will closely approximate that of tetraethylene pentamine. Finally, in preparing the compounds of this invention, where the various nitrogen atoms of the polyamine are not geometrically equivalent, several substitutional isomers are possible and are encompassed within the final product. Methods of preparation of amines and their reactions are detailed in Sidewick's "The Organic Chemistry of Nitrogen", Clarendon Press, Oxford, 1966; Noller's "Chemistry of Organic Compounds", Saunders, Philadelphia, 2nd Ed., 1957; and Kirk-Othmer's "Encyclopedia of Chemical Technology", 2nd Ed., especially Volume 2, pp. 99–116.

Preferred Hydrocarbylpoly(oxyalkylene) Alcohols

The hydrocarbyl-terminated poly(oxyalkylene) polymers which are utilized in the process of the present invention are monohydroxy compounds, i.e., alcohols, are often termed monohydroxy polyethers, or "capped" poly(oxyalkylene) glycols and are to be distinguished from the poly(oxyalkylene) glycols (diols), or polyols, which are not hydrocarbyl-terminated, i.e., not capped.

The hydrocarbyl-terminated poly(oxyalkylene) alcohols are produced by the addition of lower alkylene oxides, such as oxirane, ethylene oxide, propylene oxide, the butylene oxides, or the pentylene oxides to the hydroxy compound ROH under polymerization conditions. Methods of production and properties of these polymers are disclosed in U.S. Pat. Nos. 2,841,479 and 2,782,240, and the aforementioned Kirk-Othmer's "Encyclopedia of Chemical Technology", Volume 19, p. 507. In the polymerization reaction a single type of alkylene oxide may be empolyed, e.g., propylene oxide, in which case the product is a homopolymer, e.g., a poly(oxypropylene) propanol. However, copolymers are equally satisfactory and random copolymers are readily prepared by contacting the hydroxyl-containing compound with a mixture of alkylene oxides, such as a mixture of propylene and butylene oxides. Block copolymers of oxyalkylene units also provide satisfactory poly(oxyalkylene) polymers for the practice of the present invention. Random polymers are more easily prepared when the reactivities of the oxides are relatively equal. In certain cases, when ethylene oxide is copolymerized with other oxides, the higher reaction rate of ethylene oxide makes the preparation of random copolymers difficult. In either case, block copolymers can be prepared. Block copolymers are prepared by contacting the hydroxyl-containing compound with first one alkylene oxide, then the others in any order, or repetitively, under polymerization conditions. A particular block copolymer is represented by a poymer prepared by polymerizing propylene oxide on a suitable monohydroxy compound to form a poly(oxypropylene) alcohol and then polymerizing butylene oxide on the poly(oxypropylene) alcohol.

In general, the poly(oxyalkylene) polymers are mixtures of compounds that differ in polymer chain length. However, their properties closely approximate those of the polymer represented by the average composition and molecular weight.

The hydrocarbylpoly(oxyalkylene) alcohol is composed of oxyalkylene units containing from 2 to about 5 carbon atoms. The hydrocarbyl group contains from 1 to about 30 carbon atoms. Preferably the oxyalkylene units contain from 3 to 4 carbon atoms and the molecular weight of the hydrocarbylpoly(oxyalkylene) alcohol is from about 500 to about 5,000. The poly(oxyalkylene) polymer contains at least about 5 oxyalkylene units, preferably 8 to about 100 oxyalkylene units, more preferably about 10-100 units and most preferably 10 to about 25 such units. In general, the oxyalkylene units may be branched or unbranched. Preferably the poly(oxyalkylene) polymer chain contains at least some $C_3$-$C_5$ oxyalkylene units, more preferably, branched $C_3$-$C_5$ oxyalkylene units are present in at least sufficient number to render the final product of the process soluble in the fuel or lubricating oil composition of the present invention. This solubility condition is satisfied if the product is soluble in hydrocarbons boiling in the gasoline range at 30-2,000 ppm or in hydrocarbons of lubricating viscosity, i.e., about 35-50,000 SUS, at 100° F., at least to the extent of about 0.01 percent by weight. A poly(oxyalkylene) polymer chain composed of branched three and/or four carbon oxyalkylene units in at least sufficient amount to effect solubility in the fuel or lube composition is most preferred. The structures of the $C_3$-$C_5$ oxyalkylene units are any of the isomeric structures well known to the organic chemist, e.g., n-propylene, —CH$_2$CH$_2$CH$_2$—; isopropylene, —CH(CH$_3$)CH$_2$—; n-butylene, —CH$_2$CH$_2$CH$_2$CH$_2$—; sec.-butylene, —CH(CH$_2$CH$_3$)CH$_2$—; tert.-butylene, —C(CH$_3$)$_2$CH$_2$—; disec.-butylene, —CH(CH$_3$)CH(CH$_3$)—; isobutylene, —CH$_2$CH(CH$_3$)CH$_2$—; etc. The preferred poly(oxyalkylene) compounds are composed, at least in part, of the branched oxyalkylene isomers, particularly oxy(isopropylene), and oxy(sec.-butylene) units which are obtained from 1,2-propylene oxide and from 1,2-butylene oxide, respectively.

The hydrocarbyl moiety (R—) which terminates the poly(oxyalkylene) chain contains from 1 to about 30 carbon atoms, and is generally derived from the monohydroxy compound (ROH) which is the initial site of the alkylene oxide addition in the polymerization reaction. Such monohydroxy compounds are preferably aliphatic or aromatic alcohols of from 1 to about 30 carbon atoms, more preferably an alkanol or an alkylphenol, and most preferably an alkylphenol wherein the alkyl is a straight or branched chain of from 1 to about 24 carbon atoms. One such preferred alkyl group is obtained by polymerizing propylene to an average of 4 units and has the common name of propylene tetramer. The preferred material may be termed either an alkylphenylpoly(oxyalkylene) alcohol or a polyalkoxylated alkylphenol.

Preferred Products

Th complexity of the reaction products of the present invention mitigates against its complete expression in a single chemical name or structural formula, but it is adequately defined by the nature and mol ratios of the reactants which form the final reaction product of the process. Certain components of the final product have been identified. These identified components comprise hydrocarbylpoly(oxyalkylene) ureylene carbamates, including hydrocarbylpoly(oxyalkylene) ureylene aminocarbamates, and a preferred class of novel ureylene carbamates identified by structural formula. Hydrocarbylpoly(oxyalkylene) imidazolidones have also been identified in the reaction product when the polyamine is ethylene diamine.

The hydrocarbylpoly(oxyalkylene) ureylene carbamates of the present invention have molecular weights of from about 600 to about 10,000, preferably from about 1,000 to about 5,000, and are composed of a hydrocarbylpoly(oxyalkylene) polymer bound through a carbamate linkage, i.e.,

(wherein the oxygen atom is the terminal hydroxyl oxygen of the poly(oxyalkylene) alcohol, the carbonyl group, —C(O)— is provided by the coupling agent phosgene, and the N atom is that of the polyamine) to a polyamine component. The polyamine component is itself one of two or more polyamine components sequentially bound to each other through ureylene linkages, i.e.,

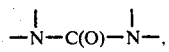

(wherein each nitrogen is a primary or secondary amino nitrogen atom of a polyamine reactant and the carbonyl group —C(O)— is provided by the coupling agent phosgene). Preferably, 2–10 such polyamine components are bound together through ureylene linkages. The ureylene carbamate chain terminates in either a free-amino group (i.e., a hydrocarbylpoly(oxyalkylene) ureylene aminocarbamate) or, in another carbamate linkage to a hyrocarbylpoly(oxyalkylene) polymer. Among the aforementioned polyamine components, those preferred for the production of ureylene carbamates are those having two or more primary or secondary amine nitrogen atoms available for reaction with phosgene, for example, the polyalkylene polyamines, including substituted polyalkylene polyamines, particularly the lower polyalkylene polyamines.

A preferred hydrocarbylpoly(oxyalkylene) ureylene carbamate product of the process of the present invention is the ureylene aminocarbamate having the following formula:

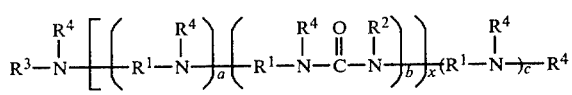

in which R' is the same or different alkylene or monohydroxy substituted alkylene radical of 2 to 6 carbon atoms, two $R^4$ groups attached to two nitrogen atoms connected by an $R^1$ group, taken together with said two nitrogen atoms and said $R^1$ group, may form a 5 or 6-membered heterocyclic radical containing two nitrogen atoms and which may also contain a carbonyl group linking said nitrogen atoms, and the remaining $R^4$ groups are selected from the aforementioned (A), (B), (C) and (D) groups of substituents. $R^3$ is the hydrocarbylpoly(oxyalkylene) oxycarbonyl group $R+OC_gH_{2g}$-$\hat{f}O$—C(O)— wherein g is an integer of 2 to 5, j is an integer such that the molecular weight of the $R^3$ is 500 to 5,000, R is hydrocarbyl of 1–30 carbon atoms, and furthermmore, one $R^4$ and not more than one $R^4$, may also be said hydrocarbylpoly(oxyalkylene) oxycarbonyl group. $R^2$ is one of the aforementioned (A), (B), (C) or (D) substituents, preferably (A). At least sufficient of the oxyalkylene units $+OC_gH_{2g}+$ are branched chain oxyalkylene units to render said ureylene carbamate soluble in fuel or lubricating oil compositions, and a is an integer 0 to 5, b is an integer 1 to 3, c is an integer 1 to 5, and x is 1 or 2.

Preferred Processes

In the process of the present invention the hydrocarbylpoly(oxyalkylene) alcohol is reacted with phosgene to produce a first product comprising a hydrocarbylpoly(oxyalkylene) chloroformate. Phosgene is preferably used in excess amounts within the aforementioned limits of 1:1–1:5 mol ratio of alcohol to phosgene, preferably 1:1.1–1:2.5. Preferably without the removal of excess phosgene from said first product, said first product is reacted with polyamine in mol ratio alcohol:-polyamine of 1:1.1 to 1:20, preferably 1:5 to 1:15. If sufficient excess phosgene is present from said first step, the excess polyamine is incorporated by the second step into the carbamate via the desired ureylene linkages. Optionally, the additional phosgene is added in a third step in such amount that the total phosgene reacted in the process is in mol ratio to said alcohol, as alcohol:-phosgene, of about 1:1.1 to 1:5, preferably 1:1.1 to 1:2.5.

The reaction of the poly(oxyalkylene) monool and phosgene is usually carried out at temperatures from −10° to 100° C., preferbly in the range of 0° to 50° C.

The reaction will usually be complete within ¼ to 24 hours. Times of reaction will usually be in the range of from 2 to 24 hours. A solvent may be used in the chloroformylation reaction. Suitable solvents include benzene, toluene, etc. The reaction of the resultant chloroformate with the amine may be carried out neat or preferably in solution. Temperatures of from −10° to 200° C. may be utilized. The desired product may be obtained by water wash and stripping, usually by the aid of vacuum, of any residual solvent. The mol ratio of the basic amine nitrogen to polyether chloroformate will more preferably be in the range from about 2 to 20 mols of basic amine nitrogen per mol of chloroformate, and most preferably 5 to 15 mols of basic amine nitrogen per mol of chloroformate. The mol ratio will depend upon the particular amine and the desired ratio of polyether to amine. Since suppression of polysubstitution of the alkylene polyamines is usually desired, large mol excesses of the amine will be used. A reaction solvent is generally employed in the reaction with polyamine whenever necessary to reduce the viscosity of the reaction product. These solvents should be stable and inert to the reactants and reaction product. Preferred solvents include aliphatic or aromatic hydrocarbons. Depending on the temperature of the reaction, the particular chloroformate used, the mol ratios and the particular amine, as well as the reactant concentrations, the reaction times with polyamine may vary from less than 1 minute to 3 hours. After the reaction has been carried out for a sufficient length of time, the final reaction product mixture may be subjected to extraction with a water-hydrocarbon or water-hydrocarbon-alcohol medium to free the product from any low-molecular-weight amine salts which have formed and any unreacted alkylene polyamines. The product may then be isolated by evaporation of the solvent. Small amounts of halogen may be present as the hydrohalide salt of polyether aminocarbamates and ureylene carbamates.

As is within the scope of this invention, the process heretofore described can be carried out in several stages. For example, an aminocarbamate can be prepared from the reaction of said hydrocarbylpoly(oxyalkylene) alcohol with phosgene followed by the reaction of the chloroformate with polyamine to yield an aminocarbamate. The aminocarbamate may be reacted with excess polyamine and excess phosgene, in the aforementioned mol ratios, (or reacted with an aminoisocyanate) to yield the final product of the present invention. As described in the aforementioned Belgian Pat. Nos. 855,961 and 855,962, the prior art teaches the reaction of essentially equimolar amounts of phosgene and alcohol. Although it is recognized that excess phosgene can improve the degree of reaction with alcohol, in the prior art the excess phosgene is removed from the chloroformate product after chloroformylation has been carried out. In the present invention either excess phosgene is not removed after chloroformylation and is present for reaction during the addition of excess polyamine to the chloroformate, or else more phosgene is added to the reaction mixture in a separate step.

If an aminocarbamate is first prepared for further reaction with excess phosgene and polyamine, the solvent need not be removed prior to the reaction with the phosgene and polyamine. In this process, the polyamine used may or may not be the same amine as that used in preparing the carbamate. The polyamine in proper proportion (1 to 20, preferably 5 to 15 mols per mol of carbamate) is combined with the carbamate, and the phosgene is added. As noted, from 0.1 to 4, preferably about 0.1 to 1.5, mol of phosgene is employed per mol of the carbamate. Times and temperatures as with the carbamate preparation are suitable, i.e., temperatures of −10° to 200° C. and times of from less than 1 minute to 3 hours to complete the reaction.

The use of higher ratios of phosgene to carbamate or to chloroformate will result in a greater amount of acyclic urea containing products. This also results in the production of more of some less desirable (less effective) urea-type compounds, and the use of lower ratios of phosgene to carbamate or chloroformate is preferred. The less desirable products minimized by the use of lower ratios of phosgene include bis-poly(oxyalkylene) ureylene carbamates, and poly(oxyalkylene) ureylene imidazolidones (formed when using an amine such as ethylene diamine).

The preferred reactants, processes and products of the present invention have been described with a view to providing the most effective lubricating oil and fuel additives, not only for lower ORI, but to provide other properties and to confront other problems as well. While ORI is the major problem confronted by the additives of this invention, other desirable properties or undesirable problems of fuel and lubricating oil compositions include deposit control, sludge formation, detergency, viscosity, dispersancy, cetane, water tolerance, rust, oxidation, compatibility and interaction with motor oil additives as well as fuel components and fuel additives.

Fuel Compositions

The poly(oxyalkylene) ureylene carbamates and the product of the process of this invention, will generally be employed in a hydrocarbon distillate fuel. The proper concentration of additive necessary in order to achieve the desired detergency and dispersancy depends upon the type of fuel employed, the presence of other detergents, dispersants and other additives, etc. Generally, however, from 30 to 2000 weight parts per million, preferably from 100 to 500 ppm of the product per part of base fuel is needed to achieve the best results. When other detergents are present, a lesser amount of product may be used. For performance as a carburetor detergent only, lower concentrations, for example 30 to 70 parts per million may be preferred.

The deposit control additive may be formulated as a concentrate, using an inert stable oleophilic organic solvent boiling in the range of about 150° to 400° F. Preferably, an aliphatic or an aromatic hydrocarbon solvent is used, such as benzene, toluene, xylene or higher-boiling aromatics or aromatic thinners. Aliphatic alcohols of about 3 to 8 carbon atoms, such as isopropanol, isobutylcarbinol, n-butanol and the like, in combination with hydrocarbon solvents are also suitable for use with the detergent-dispersant additive. In the concentrate, the amount of the additive will be ordinarily at least 10 percent by weight and generally not exceed 70 percent by weight and preferably from 10 to 25 weight percent.

In gasoline fuels, other fuel additives may also be included such as antiknock agents, e.g., methylcyclopentadienyl manganese tricarbonyl, tetramethyl or tetraethyl lead, or other dispersants or detergents such as various substituted succinimides, amines, etc. Also included may be lead scavengers such as alkyl halides, e.g., ethylene dibromide. Additionally, antioxidants, metal deactivators and demulsifiers may be present.

A particularly useful additive is a fuel-soluble carrier oil. Exemplary carrier oils include nonvolatile poly(oxyalkylene) alcohols, diols and polyols; other synthetic lubricants or lubricating mineral oil. Particularly preferred carrier oils are poly(oxyalkylene) mono and polyols, such as the Pluronics marketed by BASF Wyandotte Corp., and the UCON LB-series fluids marketed by Union Carbide Corp. When used, these oils are believed to act as a carrier for the detergent and assist in removing and retarding deposits. They are employed in amounts from about 0.005 to 0.5 percent by volume, based on the final gasoline composition. Preferably, 100–5,000 ppm by weight of a fuel-soluble poly(oxyalkylene) alcohol, glycol or polyol is used as a carrier oil. In the previously described concentrate the poly(oxyalkylene) polyols are usually present in amounts of from 5 to 80 percent by weight.

Lubricating Oil Compositions

The lubricating oil compositions of the invention are useful for lubricating internal combustion engines. The lubricating oils not only lubricate the engine, but, because of their dispersancy properties, help maintain a high degree of cleanliness of the lubricated parts.

Suitable lubricating oils which can be used to prepare a lubricating oil composition or concentrate of this invention are oils of lubricating viscosity derived from petroleum or synthetic sources. The oils can be paraffinic, naphthenic, fluoro-substituted hydrocarbons, synthetic esters, polyethers, alkylbenzenes, or combinations thereof. Oils of lubricating viscosity have viscosities in the range of 35 to 50,000 SUS at 100° F., and more usually from about 50 to 10,000 SUS at 100° F.. The amount of the product of this invention which is incorporated into the lubricating oil to provide the effective amount necessary for dispersancy varies widely with the particular product used as well as the use intended for the lubricating oil composition. Other conventional additives which can be used in combination with the product of this invention include ashless dispersants such as the type disclosed in U.S. Pat. Nos. 3,172,892, 3,219,666, 3,381,022; neutral and basic calcium, barium and magnesium petrosulfonates or alkyl phenates; oxidation inhibitors, antifoam agents, viscosity index improvers, pour-point depressants, and the like, such as chlorinated wax, benzyldisulfide, sulfurized sperm oil, sulfurized terpene; phosphorus esters such as trihydrocarbon phosphites and phosphates; metal thiocarbamates such as zinc dioctyldithiocarbamate; metal phosphorus dithioates such as zinc dioctylphosphorodithioate; polyisobutene having an average molecular weight of 100,000; etc.

In general, the lubricating oil compositions will contain from about 0.01 to 20 weight percent of said oil-soluble product. More usually, the lubricating oil composition of the invention will contain from about 0.5 to about 10 weight percent of the product and more usually from about 1 to about 8 weight percent of the product of this invention.

In a second embodiment of this invention, lubricating oil additive concentrates are provided comprising from about 90 to about 20 percent of an inert stable oleophilic solvent such as oil of lubricating viscosity and from about 10 to about 80 weight percent of the product of this invention. Typically, the concentrates contain sufficient diluent to make them easy to handle during shipping and storage. Preferably, the diluent is an oil of lubricating viscosity so that the concentrate may be readily mixed with lubricating oils to prepare lubricating oil compositions. Suitable lubricating oils which can be used as diluents typically have viscosities in the range from about 35 to about 1000 Saybolt Universal Seconds (SUS) at 100° F., although any oil of lubricating viscosity can be used.

EXEMPLIFICATION

The following examples are presented to illustrate specific embodiments of the practice of this invention and should not be interpreted as limitations upon the scope of the invention.

EXAMPLE 1—Reaction of Phosgene with Poly(oxypropylene) Moncol

A 99 g (1.0 mol) portion of phosgene was condensed into 750 ml of toluene at 0° C. A 450 g (0.17 mol) portion of monobutyl poly(oxypropylene) alcohol having a molecular weight of about 2400 was added as a slow stream to the phosgene-toluene mixture over a period of ½ hour while maintaining the temperature at 0°–10° C. 200 ml of benzene were added. The temperature was raised to 80° and excess phosgene and benzene were distilled from the product. A small sample was taken; toluene was evaporated from it. Infrared analysis showed a strong chloroformate absorption at 1785 $cm^{-1}$.

EXAMPLE 2—Reaction of Poly(oxypropylene) Chloroformate with Amine

One half of the product from Example 1 (in toluene solution) was added at room temperature to 154 g (1.5 mols) of diethylenetriamine in 500 ml of toluene. Immediate precipitation of an amine hydrochloride occurred. The mixture was stirred for one-half hour, filtered and the toluene was removed under reduced pressure. The residue was dissolved in 1½ volumes of hot n-butanol and extracted three times with 100–200 ml of hot water. The butanol was removed by vacuum providing 200 g of a product which contained 1.17% nitrogen and 0.80% basic nitrogen by ASTM D-2896. Infrared analysis revealed a typical carbamate absorption at 1725 $cm^{-1}$.

EXAMPLE 3—Preparation of Product From Poly(oxypropylene) Amino Carbamate

A poly(oxypropylene) aminocarbamate was prepared by the method of Examples 1 and 2 from a butyl-capped poly(oxypropylene) monool (MW, 1600) and ethylene diamine. The aminocarbamate (400 g, 0.25 mol) was combined with 167 ml (2.5 mols) of ethylene diamine and cooled to 5° C. 5.3 ml (0.075 mol) of phosgene was condensed and transferred into 100 ml of toluene at 0° C. The phosgene solution was added over a period of about 5 minutes to the rapidly stirred aminocarbamate-ethylene diamine mixture. An opaque white vapor appeared immediately. The pot temperature was held below 30° C. After addition was complete, the cooling was removed and the mixture was stirred for one hour. The product was extracted into 500 ml of n-butanol and washed five times with 500 ml aliquots of hot water. The toluene and n-butanol were removed under reduced pressure. The product was 233 g of a viscous, yellow liquid with an average molecular weight of 1554 and weight percent total nitrogen of 1.39% and basic nitrogen of 0.50%. This product is designated Product A.

EXAMPLE 4—Preparation of Poly(oxybutylene)

The experiment was carried out under nitrogen using anhydrous conditions. Potassium (3.52 g, 0.09 mol) was added to 79 g (0.3 mol) of a phenol alkylated with propylene tetramer. The mixture was stirred and heated to 80° C. for 20 hours, until the potassium was no longer visible. Freshly distilled 1,2-epoxy-butane (646 ml, 7.5 mols) was added to this stirred solution and the mixture was refluxed for 64 hours. At the end of this time the pot temperature had reached 158° C. The product was extracted into 500 ml of n-butanol and washed with 400 ml of hot water. The solvent was removed under reduced pressure, yielding 560 g of a viscous liquid of molecular weight 1550.

EXAMPLE 5—Preparation of Poly(oxybutylene) Chloroformate

The reaction was carried out under nitrogen using anhydrous conditions. Phosgene (60 ml, 0.84 mol) was condensed into 500 ml of toluene at 5° C. The polymer from Example 4 (560 g, 0.36 ml) was added dropwise to the cooled phosgene solution. The reaction mixture was stirred without cooling for 1 hour after addition was complete. The IR spectrum of a sample of the product which had been treated with nitrogen to remove phosgene showed a strong carbonyl absorption at 1785 $cm^{-1}$. Nitrogen was bubbled through the solution for an additional 2 hours to remove phosgene, but not all the excess phosgene was removed.

EXAMPLE 6—Preparation of Product

The reaction was carried out under nitrogen. Ethylene diamine (374 ml, 5.6 mols) was cooled in an ice bath. The product of Example 5 was diluted to 3500 ml and added as quickly as possible to the rapidly stirred ethylene diamine while maintaining the pot temperature below 30° C. After the addition was complete, the ice bath was removed and the mixture was stirred for an additional hour. The product was extracted into 700 ml of n-butanol and washed four times with 500 ml aliquots of hot water. The solvent was removed under reduced pressure, yielding an orange-brown, gel-like material of average molecular weight 2166, containing 0.29% basic nitrogen and 1.64% total nitrogen. This was called Product B.

EXAMPLE 7

Following the procedures of Example 3, a poly(oxypropylene) product (derived from butylpoly(oxypropylene) ethylene diamine carbamate and ethylene diamine) was prepared. This material (Product C) had an average molecular weight of 1565, 0.43 weight percent basic nitrogen, and 1.75 weight percent total nitrogen.

EXAMPLE 8

Following the procedures and employing the starting materials of Examples 4, 5 and 6, a alkylphenyl poly(oxybutylene) product was prepared (Product D) having an average molecular weight of 1332, 0.51 weight percent basic nitrogen and 2.03 weight percent total nitrogen. The only difference in procedure was that no nitrogen was bubbled through the phosgene/chloroformate solution.

EXAMPLE 9

Following the general procedure and starting materials of Examples 5 and 6, a alkylphenyl poly(oxypropylene) product was prepared from a starting polymer of about 1300 molecular weight; the product had an average molecular weight of 2197, 0.12% basic nitrogen and 1.68% total nitrogen (Product E).

In the following tests the poly(oxyalkylene) products were blended in gasoline and their deposit control capacity tested in an ASTM/CFR Single-Cylinder Engine Test.

In carrying out the tests, a Waukesha CFR single-cylinder engine is used. The run is carried out for 15 hours, at the end of which time the intake valve is removed, washed with hexane and weighed. The previously determined weight of the clean valve is subtracted from the weight of the valve. The differences between the two weights is the weight of the deposit with a lesser amount of deposit measured connoting a superior additive. The operating conditions of the test are as follows: water jacket temperature 100° C. (212° F.); manifold vacuum of 12 in Hg, intake mixture temperature of 50.2° C. (125° F.); air-fuel ratio of 12; ignition spark timing of 40° BTC; engine speed is 1800 rpm; the crankcase is a commercial 30 W oil. The amount of carbonaceous deposit in milligrams on the intake valves is measured and reported in the following Table I.

The base fuel tested in the above test is a regular octane unleaded gasoline containing no fuel deposit control additive. The base fuel is admixed with varying amounts of the deposit control additives. Products A', B', and E' are the poly(oxyalkylene) aminocarbamates comparing respectively to Products A, B, and E.

TABLE I

Intake Valve Deposit Tests[1]

| Additive, Carrier Description | ppm | Average Washed Deposit, mg 11A Engine | 12A Engine |
|---|---|---|---|
| Base Fuel | — | 125–175[2] | 125–175[2] |
| Product A | 200 | 49 | 154 |
| PPG-1450[4] | 100 | | |
| Product E | 200 | 21, 19 | 14, 33 |
| PPG-1450 | 100 | | |
| Product E | 300 | 13 | 38 |
| PPG-1450 | 150 | | |
| Product A' | 200 | 165 | 242 |
| PPG-1450 | 100 | | |
| Product E' | 200 | 175, 153 | 126, 136 |
| PPG-1450 | 100 | | |
| Product E' | 300 | 82 | 27 |
| PPG-1450 | 100 | | |

[1]Single evaluations unless noted.
[2]Range of several runs.
[3]Average of 4 runs.
[4]The designation PPG-1450 refers to a monobutyl-capped poly (propylene glycol) of about 1450 molecular weight.

The above results show the significant reduction in valve deposits achieved compared with base fuel. They also show that each of the products of the present invention is superior in deposit control to the corresponding aminocarbamate.

The test for evaluating the ability of fuel additives to control carburetor deposits employs a 1973 model year, 240 CID, 6-cylinder Ford engine. The internal bore of the carburetor throttle body is equipped with a thin, removable aluminum sleeve. The difference between sleeve weights determined before and after an engine run represents the change in amount of surface deposit occurring during that run.

For additive evaluation, two test phases are run as set forth in Table II.

TABLE II

Carburetor Deposit Test Procedure

1. Dirty-Up Phase (Starting with Clean Sleeve)

| | |
|---|---|
| Objective: | Establish deposits on carburetor sleeve. |
| Duration: | 15 hours. |
| Operating Cycle: | 7 minutes moderate load and speed, 4 minutes idle. |
| Engine Setup: | Crankcase blowby gases routed to carburetor air inlet. |
| Fuel: | Deposit-forming fuel containing heavy FCC component. |
| Evaluation: | Sleeve weights are determined at the beginning and end of the dirty-up phase, and sleeve deposits are rate visually on a scale of 0 to 10 (10 = clean). |

2. Cleanup Phase (Begins with Sleeve Deposits Formed During Dirty-UP Phase

| | |
|---|---|
| Objective: | Measure additive performance in cleaning up deposits. |
| Duration: | 4 hours. |
| Operating Cycle: | Same as dirty-up phase. |
| Engine Setup: | Crankcase blowby cases diverted from carburetor inlet-EGR shutoff. |
| Fuel: | Commercial-type gasoline containing additive under test. |
| Evaluation: | The sleeve is reweighed. Differences between initial and final values represent additive effectiveness. |

Table III presents average values for the performance of product additives of the present invention. Also, presented are values for a commercial deposit control additive having recognized performance in the field. Deposit level changes with a commercial-type unleaded gasoline without additive are also shown.

TABLE III

Carburetor Test Results

| | Concentration. ppm | Average Additive Performance Deposit Weight Reduction, % |
|---|---|---|
| Product A | 200 | 72 |
| Product B | 200 | 89 |
| Commercial deposit control Additive | 150 | 91 |
| None | — | 63 |

These data show that the products of the present invention show activity as carburetor deposit control additives.

In order to demonstrate the capacity of the additives of this invention to function in fuels for internal combustion engines without contributing significantly to engine ORI, "octane requirement increase", the additives were subjected to thermogravimetric analysis. Compounds showing low TGA values have been shown to show also very low ORI values in laboratory engine tests, as well as in employee automobile engine tests conducted under ordinary driving conditions.

Thermogravimetric analysis is performed in a 951 Thermal Gravimetric Analyzer manufactured by the Du Pont Company. A small weighed sample of the material to be analyzed is placed in the Analyzer and exposed to a flow of 60 ml of air per minute at the specified temperature and for a specified period. 30 minute exposures at 200° C. and at 290°–300° C. were employed. The results of the test are set forth in Table IV following:

TABLE IV

| | Thermogravimetric Analysis of Poly(oxyalkylene) Amine Esters | |
|---|---|---|
| Product | Weight Remaining, % 30 min. at 290°–300° C. | Weight Remaining, % 30 min. at 200° C. |
| A | — | 47 |
| B | 1 | 79 |
| C | — | 59 |
| D | — | 82 |
| Z | 50–60 | 100 |

Compound Z is a commercially available nitrogen-containing deposit control additive which has been shown to yield higher ORI values. These data show that the poly(oxyalkylene) products of this invention have low TGA values comparable to those compounds which are known to have low ORI values, consequently, they are expected to have comparably low ORI values.

Although many specific embodiments of the invention have been described in detail, it should be understood that the invention is to be given the broadest possible interpretation within the terms of the following claims.

What is claimed is:

1. A fuel compostion comprising a major amount of hydrocarbons boiling in the gasoline range, and from 30 to 2,000 ppm of a hydrocarbylpoly(oxyalkylene) ureylene carbamate of molecular weight from about 600 to 10,000; wherein said hydrocarbylpoly(oxyalkylene) moiety is composed of oxyalkylene units selected from 2 to 5 carbon oxyalkylene units of which at least a sufficient number are branched chain oxyalkylene units to render said carbamate soluble in said fuel composition, and said hydrocarbyl group contains from 1 to 30 carbon atoms.

2. A fuel composition according to claim 1 wherein said hydrocarbylpoly(oxyalkylene) ureylene carbamate contains at least one basic nitrogen atom in a primary or secondary amino nitrogen group.

3. A fuel composition according to claim 1 wherein said hydrocarbylpoly(oxyalkylene) moiety consists of 1 to 2 hydrocarblpoly(oxyalkylene) polymers.

4. A fuel composition according to claim 1 wherein each of said oxyalkylene units contains 3-4 carbon atoms.

5. A fuel composition according to claim 4 wherein each of said oxyalkylene units is oxybutylene.

6. A fuel composition according to claim 1 wherein said hydrocarbyl group is butyl or alkylphenyl.

7. A fuel composition according to claim 6 in which said hydrocarbyl group is alkylphenyl.

8. A fuel composition according to claim 1 in which said hydrocarbylpoly(oxyalkylene) moiety has a molecular weight from about 500 to 5,000.

9. A fuel composition according to claim 1 in which said hydrocarbylpoly(oxyalkylene) ureylene carbamate has a molecular weight of about 1,000 to 5,000.

10. A fuel composition according to claim 1 in which said ureylene carbamate is derived from a polyamine having from 2 to 12 amine nitrogen atoms and 2-40 carbon atoms, with a carbon:nitrogen ratio of about 1:1 to 10:1.

11. A fuel composition according to claim 10 in which said polyamine is a substituted polyamine with substituents selected from (A) hydrogen, (B) hydrocarbyl groups of from 1 to about 10 carbon atoms, (C) acyl groups of from 2 to about 10 carbon atoms, and (D) monoketo, monohydroxy, mononitro, monocyano, lower alkyl and lower alkoxy derivatives of (B) and (C).

12. A fuel composition according to claim 10 in which said polyamine is a polyalkylene polyamine wherein each alkylene contains from 2 to 6 carbon atoms and said polyamine contains fromm 2 to 12 nitrogen atoms and from 2 to 24 carbon atoms.

13. A fuel composition according to claim 12 in which said polyalkylene polyamine is selected from ethylene diamine, polyethylene polyamine, propylene diamine, and polypropylene polyamine.

14. A fuel composition according to claim 12 in which said polyalkylene polyamine is ethylene diamine.

15. A fuel composition according to claim 1 in which said hydrocarbylpoly(oxyalkylene) ureylene carbamate is alkylphenyl polyoxyalkylene ureylene aminocarbamate.

16. A fuel composition according to claim 1 in which said hydrocarbylpoly(oxyalkylene) ureylene carbamate is butylpoly(oxyalkylene) ureylene aminocarbamate.

17. A fuel composition comprising a major portion of hydrocarbon boiling in the gasoline range and a minor portion sufficient to effect deposit control of the deposit control additive obtained by reacting, in a first step, a hydrocarbylpoly(oxyalkylene) alcohol with phosgene in mol ratio of about 1:1 to about 1:5 to obtain a first product; reacting, in a second step, said first product with a polyamine in a mol ratio of said poly(oxyalkylene) alcohol to polyamine of from about 1:1. to about 1:20 to obtain a second product; and reacting, in a third step, said second product with phosgene in such amount that the total phosgene reacted in the steps of the process is in mol ratio to said hydrocarbylpoly(oxyalkylene) alcohol of from about 1.1:1 to about 5:1; wherein said hydrocarbylpoly(oxyalkylene) alcohol is composed of oxyalkylene units selected from 2 to 5 carbon oxyalkylene units, said hydrocarbyl group contains from 1 to 30 carbon atoms, said polyamine contains from 2 to 40 carbon atoms and from 2 to 12 amine nitrogen atoms, and said polyamine consists at least in part of polyamine containing at least 2 primary or secondary amine nitrogen atoms.

18. A fuel composition comprising a major portion of hydrocarbon boiling in the gasoline range and a minor portion sufficient to effect deposit control of the deposit control additives having the formula:

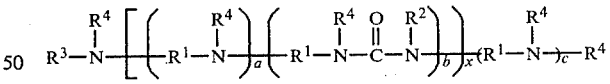

in which $R^1$ is the same or different alkylene or monohydroxy substituted alkylene radical of 2 to 6 carbon atoms, two $R^4$ groups attached to two nitrogen atoms connected by an $R^1$ group, taken together with said two nitrogen atoms and said $R^1$ group, may form a 5 or 6-membered heterocyclic radical containing two nitrogen atoms and may contain a carbonyl group linking said nitrogen atoms; the remaining $R^4$ groups being selected from the substituents selected from (A) hydrogen, (B) hydrocarbyl groups of from 1 to about 10 carbon atoms, (C) acyl groups of from about 2 to about 10 carbon atoms, and (D) monoketo, monohydroxy, mononitro, monocyano, lower alkyl and lower alkoxy derivatives of (B) and (C); $R^3$ is the hydrocarbylpoly(oxyalkylene) oxycarbonyl group, $R+OC_gH_{2g}$-$)_j$-O-C(O)-, wherein g is an integer of from 2 to 5, j is an integer such that the molecular weight of $R^3$ is 500 to 5,000, R is hydrocarbyl of 1–30 carbon atoms, and one $R^4$ may also be said hydrocarbylpoly(oxyalkylene) oxycarbonyl group; $R^2$ is one of the aforementioned (A), (B), (C) or (D) substituents; and at least sufficient of the oxyalkylene units, $+OC_gH_{2g}+$ are branched chain oxyalkylene units to render said ureylene carbamate soluble in a fuel or lubricating oil composition; a is an integer 0 to 5, b is an integer 1 to 3, c is an integer 1 to 5, and x is 1 or 2.

19. A fuel composition according to claim 18 wherein g is 3 or 4.

20. A fuel composition according to claim 18 in which a is 0 and b and x are 1.

21. A fuel composition according to claim 18 wherein the $R^4$ groups are H.

22. A fuel composition according to claim 18 which $R^1$ is propylene or ethylene.

23. A fuel composition according to claim 18 wherein R is an alkylphenyl group having from 7 to 30 carbon atoms.

* * * * *